US005889107A

United States Patent [19]
Jakob et al.

[11] Patent Number: 5,889,107
[45] Date of Patent: Mar. 30, 1999

[54] POLYVINYL ESTER DISPERSION WITH METAL SALT HYDROSOLS AS PRECIPITATION BASIS

[75] Inventors: Martin Jakob, Kelkheim; Heinz Hennemann, Oberneisen; Volker Matz, Frankfurt, all of Germany

[73] Assignee: Clariant GmbH, Frankfurt, Germany

[21] Appl. No.: 930,096

[22] PCT Filed: May 10, 1996

[86] PCT No.: PCT/EP96/01999

§ 371 Date: Nov. 12, 1997

§ 102(e) Date: Nov. 12, 1997

[87] PCT Pub. No.: WO96/36648

PCT Pub. Date: Nov. 21, 1996

[30] Foreign Application Priority Data

May 15, 1995 [DE] Germany .................. 195 17 777.0

[51] Int. Cl.⁶ ........................................ C08K 3/10
[52] U.S. Cl. ................................................ 524/783
[58] Field of Search .................................. 524/783

[56] References Cited

U.S. PATENT DOCUMENTS

| | | | |
|---|---|---|---|
| 2,455,937 | 12/1948 | Lowe | 260/29.2 |
| 3,301,809 | 1/1967 | Goldberg et al. | 260/29.6 |
| 3,941,730 | 3/1976 | Solenberger | 260/17 R |
| 4,085,074 | 4/1978 | Woo | 260/17 R |

FOREIGN PATENT DOCUMENTS

| | | |
|---|---|---|
| 0 069 301 A1 | 1/1983 | European Pat. Off. . |
| 0 337 672 B1 | 10/1989 | European Pat. Off. . |
| 0 433 957 A2 | 6/1991 | European Pat. Off. . |
| 2620738 C2 | 4/1983 | Germany . |
| 3942628 A1 | 6/1991 | Germany . |

OTHER PUBLICATIONS

"Polyvinyl Acetate Emulsions for Adhesives", Handbook of Adhesives, 3rd Edition, Chapter 21, Van Nostrand Reinhold, New York, 1990.

"The Chemistry of PVA", Wood Adhesives—Chemistry and Technology, vol. 1, Chapter 7, Marcel Dekker, New York, 1983.

"Polyvinyl Acetate Wood Adhesives", Wood Adhesives—Chemistry and Technology, vol. 2, Chapter 2, Marcel Dekker, New York, 1989.

"Recent Advances in the Preparation of Latexes", J.W. Vanderhoff, Chemical Engineering Science, vol. 48, No. 2, pp. 217, 1993.

"Microencapsulation de silices par des polymers", Andre Revillon et al., Double Liason, 431–432, 285 (1991).

"Structural Aspects of Zirconium Chemistry", Abraham Clearfield, Rev. Pure and Appl. Chem. 14, 91 (1964).

Primary Examiner—Edward J. Cain
Attorney, Agent, or Firm—Philip P. McCann

[57] ABSTRACT

Polyvinyl ester dispersions comprising a hydrosol of a complex salt of a metal from subgroup 4 of the Periodic Table of the Elements with an organic α-hydroxy and/or α-oxo acid as seed base, which hydrosol comprises a surface-active substance, are suitable as adhesive and coating compositions.

11 Claims, No Drawings

POLYVINYL ESTER DISPERSION WITH METAL SALT HYDROSOLS AS PRECIPITATION BASIS

The invention relates to hydrosols of metal complex salts, comprising surface-active substances, and to a special process for the free-radical emulsion polymerization of vinyl esters in the presence of these hydrosols as seed base. The invention additionally relates to the use of polyvinyl ester dispersions prepared in this way as adhesives for porous or semiporous substrates.

Aqueous dispersions of polyvinyl esters, especially those of polyvinyl acetate, are used as so-called white glues for bonding wood and other porous substrates. Adhesives of this kind have been described in the literature, for example in Handbook of Adhesives, 3rd edition, chapter 21, Van Nostrand Reinhold, New York, 1990 and in Wood Adhesives—Chemistry and Technology, volume 1, chapter 7, Marcel Dekker, New York, 1983.

These adhesives are usually prepared by free-radical emulsion polymerization of the vinyl esters in the presence of polymeric stabilizers, so-called protective colloids, especially polyvinyl alcohol. A review of this process, which is treated extensively in the technical literature, can be found, for example, in Wood Adhesives—Chemistry and Technology, volume 2, chapter 2, Marcel Dekker, New York, 1989.

The emulsion polymerization of vinyl esters, especially vinyl acetate, in the presence of polyvinyl alcohol usually produces dispersions of relatively high viscosity. Also, compared with dispersions stabilized only with the aid of pure emulsifiers, the particle-size distributions are broader. Depending on the polymerization process, the type of initiator, the type of stabilizer and other parameters it is also common, furthermore, to observe instances of particle agglomeration. This phenomenon is the cause in particular of a further increase in the viscosity of the dispersions, going as far as to produce a pastelike consistency and to impair flow. This also causes a loss in shear stability and, in general, adversely affects the reproducible preparation of dispersions within narrow viscosity limits.

A subgroup of polyvinyl ester dispersions is formed by those whose adhesive bonds are of enhanced water resistance. In these dispersions, the hydrophilicity of the polyvinyl alcohol used as protective colloid is often reduced by copolymerization with vinyl compounds having a crosslinking action, such as N-methylol(meth)acrylamide.

Such a method is proposed, for example, in the documents U.S. Pat. No. 3,301,809, DE-C 26 20 738 and DE-A 39 42 628. In combination with acidic curing agents, such as aqueous mineral acids or acidic metal salts, for example aqueous solutions of aluminum chloride, water-resistant adhesives are obtained.

A known disadvantage of the process is that the copolymerization of increasing quantities of the crosslinking agent, N-methylol(meth)acrylamide, results in a further drastic increase in viscosity being observed. Moreover, on storage, the dispersions—especially in the acid-catalyzed form—tend to show an increase in viscosity and structure. The pot life of the acid-catalyzed glue formulations, therefore, is usually short.

The documents DE-C 26 20 738 and DE-A 39 42 628 describe a two-stage polymerization process in which part of a monomer mixture is included in the aqueous initial charge and part is metered in. The monomers involved are principally vinyl esters of acetic acid, pivalic acid and ®Versatic acids (α,α-dialkylcarboxylic acids, Shell-Chemie) and also N-methylolacrylamide. Depending on the nature of the vinyl esters and the nature of the acidic catalysts added subsequently, glue formulations are obtained which have pot lives of at least 4 weeks.

In U.S. Pat. No. 4 085 074, volatile nitrogen bases such as ammonia, mono-, di- or trialkyl(ol)amines, especially triethanolamine, are proposed as crosslinking inhibitors for the acidic metal salts such as aluminum chloride. The bases are added to the glue formulations subsequently. The stability of formulations modified in this way, on storage, exceeds 3 months, although their viscosities prior to storage, at <1.5 Pa•s, are distinctly below the current market requirements for such systems, which are at least 7 Pa•s. Furthermore, dispersions comprising nitrogen bases frequently show a tendency to undergo yellowing on storage.

Moreover, both of the abovementioned attempts at solutions do not solve the problem of the drastic increase in the viscosities of polyvinyl ester dispersions prepared using increasing quantities of N-methylol(meth)acrylamide.

The processes employed in DE-C 26 20 738 and DE-A 39 42 628 apparently comprise a graft reaction onto a particle seed which is produced during the initial phase of polymerization and consists of a polymer which has already been pre-crosslinked and is stabilized with polyvinyl alcohol.

The fundamental principle of a seed polymerization of conventional procedure is that, prior to emulsion polymerization in the aqueous liquor, a certain quantity of a dispersion which has already been prepared in a prior process step is introduced as initial charge. In this way, in the presence of already existing particles, the polymerization is carried out with controlled quantities of emulsifier and initiator, thereby making it possible to obtain specific particle-size distributions (see J. W. Vanderhoff, Chem. Engin. Sc. 48, 203 (1993)). A disadvantage of such a procedure, however, is that two polymerization steps are necessary in order to prepare such a dispersion.

Moreover, the literature includes numerous variants of seed polymerizations in which, instead of a polymer seed latex, an inorganic particle seed, for example a pigment, is introduced prior to emulsion polymerization. Examples of such particles are finely divided calcium carbonate, titanium dioxide or silica gel particles, which are encapsulated during polymerization by the polymer which grows on them. A review of the literature is given by A. Revillon et al. in Double Liaison 431–432, 285 (1991).

EP-B 0 337 672 describes the emulsion polymerization of vinyl esters in the presence of a high proportion of titanium dioxide pigment particles using a redox initiator system, predominantly in the presence of polymeric stabilizers such as hydroxyethylcellulose and polyacrylic acid, and in the presence of an anionic emulsifier, with the result that the pigment particles are not encapsulated but are in the form of discrete particles, surrounded by polymer particles, in the form of knot-like formations. The dispersions are used as a surface-coating material with improved opacity and a relatively high-shear viscosity.

From the literature (A. Clearfield, Rev. Pure and Appl. Chem. 14, 91 (1964)) it is known that stable complex compounds with zirconium(IV) and bidentate oxygen ligands are obtainable which precipitate in gelatinous, amorphous form from the acidic aqueous solutions of salts of zirconium(IV) following the addition of low molecular weight α-hydroxycarboxylic acids, for example glycolic acid. These compounds also comprise chelate complexes in which the α-hydroxycarboxylic acid occurs as a bidentate oxygen ligand.

The object of the present invention was to develop a process of free-radical emulsion polymerization for the preparation of polyvinyl ester dispersions stabilized predominantly with protective colloids, such as polyvinyl alcohol, which process provides for a reduced tendency toward particle agglomeration and thereby an improved rheological control of the end products and imparts lower latex viscosities, even when relatively large quantities of crosslinking comonomers, such as N-methylol(meth) acrylamide, are copolymerized, and, following the addition of acidic crosslinking catalysts, for example aqueous solutions of aluminum chloride, gives the glue formulations catalyzed in this way a prolonged stability on storage.

It has now surprisingly been found that both aspects of this object can be achieved by a novel process of emulsion polymerization which comprises carrying out a seed polymerization by initially charging, to the aqueous polymerization liquor prior to polymerization, a colloidally disperse complex salt of an organic acid with a metal from subgroup 4 of the Periodic Table of the Elements, especially zirconium, as particle seed which is stabilized with at least one surface-active substance, especially polyvinyl alcohol.

The invention provides a hydrosol of a complex salt of a metal from subgroup 4 of the Periodic Table of the Elements, especially zirconium, with an organic $\alpha$-hydroxy and/or $\alpha$-oxo acid, which hydrosol comprises a surface-active substance, preferably a predominantly polymeric stabilizer, especially polyvinyl alcohol.

The particle sizes of the hydrosols which are suitable as particle seed for a subsequent emulsion polymerization are usually in the range from 200 nm to 5 $\mu$m. Under the electron microscope, the hydrosol particles reveal themselves in turn to be aggregates of even smaller, primary particles, with a size of about 20 nm.

The stabilizer preferably present in the hydrosols according to the invention is polyvinyl alcohol with a degree of hydrolysis of from 60 to 100 mol %, in particular from 70 to 98 mol %, whose 4% strength by weight aqueous solutions have viscosities which are preferably from 2 to 70 mPa·s at 20° C. A suitable polyvinyl alcohol is preferably the same one which is used later in the aqueous polymerization liquor to stabilize the polyvinyl ester dispersion. It is therefore also possible to employ different products with different degrees of hydrolysis and molecular weights.

If different or additional polymeric stabilizers are used in the colloidally disperse complex salts, suitable protective colloids are those which are devoid of free carboxyl groups or other functional groups with a high propensity to form complexes with zirconium ions. Examples which may be mentioned in this context are hydroxyethylcellulose, starch, starch derivatives, dextrin and polyvinylpyrrolidone.

The additional use of small quantities of anionic, non-ionic or cationic emulsifiers is permissible. Preferably, non-ionic emulsifiers such as ethoxylated fatty alcohols, for example, are additionally used. The quantity thereof is preferably such that their overall quantity in the subsequent polymerization, based on the mass of the monomers, is from 0 to 3% by weight, preferably from 0.005 to 2% by weight.

The mass of the surface-active substances used to stabilize the complex compound is preferably such that from 0.5 to 100 g, in particular from 1 to 20 g and, with particular preference, from 2 to 5 g of surface-active substances are used per millimole of zirconium.

The hydrosols according to the invention comprise at least one element from subgroup 4 of the Periodic Table of the Elements, especially zirconium. It is also possible for mixtures of an element from subgroup 4 with other elements from this group or with other metallic elements to be present.

The $\alpha$-hydroxy and/or $\alpha$-oxo acids present in the hydrosols according to the invention are preferably those which in an acidic medium form insoluble complex compounds with water-soluble Zr(IV) salts. Acids which are particularly suitable in accordance with the invention, which carry a hydroxyl group in the position $\alpha$ to at least one carboxyl group, are glycolic acid, acrylamidoglycolic acid, lactic acid, citric acid, mandelic acid and tartaric acid. Examples of other preferably suitable compounds which in addition to a carboxyl group have a carbonyl group in the $\alpha$-position to it, and which therefore, in aqueous equilibrium in hydrated form, have two geminal hydroxyl groups in the $\alpha$-position with respect to the carboxyl group, are glyoxylic acid and pyruvic acid. Glyoxylic acid in particular is especially suitable, and preferred, for the preparation of a hydrosol according to the invention as particle seed for the subsequent emulsion polymerization.

The molar ratio between the organic $\alpha$-hydroxy and/or $\alpha$-oxo carboxylic acids used and the aqueous Zr(IV) salts is of great significance for the effects subsequently observed during emulsion polymerization on the particle-size distribution of the dispersions. In this context, the molar ratio of carboxylic acid to zirconium should preferably be from 0.001 to 4, in particular from 0.05 to 2 and, with particular preference, from 0.08 to 1.2.

The present invention also provides a process for the preparation of a hydrosol of a complex salt of a metal from subgroup 4 of the Periodic Table of the Elements, especially zirconium, with an organic $\alpha$-hydroxy and/or $\alpha$-oxo acid by precipitation, from homogeneous aqueous solution, of a water-soluble salt of said metal by adding an organic $\alpha$-hydroxy and/or $\alpha$-oxo acid or an aqueous or organic solution of this organic acid in the presence of a surface-active substance, preferably a predominantly polymeric stabilizer, especially polyvinyl alcohol.

The Zr(IV) complex salt hydrosols stabilized very preferably with polyvinyl alcohol which are suitable as particle seed for a subsequent emulsion polymerization are prepared, for example, in a simple manner by first preparing an aqueous solution of polyvinyl alcohol of defined concentration. During the preparation of the hydrosol the concentration of the polyvinyl alcohol solution is preferably from 1 to 20% by weight. The concentration of the solution is in particular the same as that possessed subsequently by the polymerization liquor used. The $\alpha$-hydroxycarboxylic acid or the $\alpha$-oxo-carboxylic acid is dissolved in this solution with stirring, and an aqueous solution of an acidic, water-soluble Zr(IV) salt is added. The acidic, water-soluble Zr(IV) salts used comprise, for example, aqueous solutions of zirconium oxychloride, zirconium nitrate, zirconium orthosulfate and zirconium acetate. Since the acidity of zirconium acetate is less than that of the highly acidic salts of zirconium oxychloride, zirconium nitrate and zirconium orthosulfate, the former is particularly preferred, since after adding this solution the pH is already at a level, suitable for the subsequent emulsion polymerization, of between 3 and 5. Of course, it is also possible to raise the pH of the hydrosol to the required values after its preparation, by the use of suitable neutralizing agents, such as dilute sodium hydroxide solution. In the case of zirconium acetate this gives rise, owing to the acetic acid liberated, to a buffer system which when used in dispersions suppresses any viscosity increases caused purely by changes in pH. The hydrosols prepared with other salts can be modified by adding appropriate buffer systems. After a period of time which depends on the reaction temperature, the hydrosol is formed, which can be recognized by the solution beginning to take on a milky-cloudy consistency. The suitable reaction temperature is from 20° to 90° C., preferably from 30° to 80° C., in particular from 40° to 60° C. The hydrosol usually forms in this temperature range within minutes. It can then be added to a polymerization liquor or, preferably, can itself be used in a one-pot process as polymerization liquor for the subsequent emulsion polymerization.

By means of the type and molecular weight of the stabilizer used, by its concentration in the solution and therefore by the mass ratio of the stabilizer relative to the complex compound, and also by means of the stirring speed during the reaction, it is possible to vary the particle sizes of the hydrosols. In this context, especially when polyvinyl alcohol is used, increasing molecular weights and the concentration in the solution and increasing the stirring speed results in a marked reduction being observed in the particle sizes of the hydrosols.

The invention additionally provides a polyvinyl ester dispersion which is obtainable by emulsion polymerization of at least one vinyl ester monomer and, if desired, further copolymerizable monomers in the presence of a hydrosol of a complex salt of a metal from subgroup 4 of the Periodic Table of the Elements, especially zirconium, with an organic α-hydroxy and/or α-oxo acid, which hydrosol comprises a surface-active substance, preferably a predominantly polymeric stabilizer, especially polyvinyl alcohol.

The monomer base for the homo- or copolymeric polyvinyl ester dispersion according to the invention can be formed by vinyl formate, vinyl acetate, vinyl propionate, vinyl isobutyrate, vinyl pivalate, vinyl 2-ethyl-hexanoate, vinyl esters of saturated α-branched mono-carboxylic acids having 9 to 10 carbon atoms in the acid radical, vinyl esters of longer-chain saturated or unsaturated fatty acids, for example vinyl laurate and vinyl stearate, and also vinyl esters of benzoic acid and substituted derivatives of benzoic acid, such as vinyl p-tert-butylbenzoate. Among these, particular preference is given to vinyl acetate. The vinyl esters mentioned may also be present in combination in the polyvinyl ester. The proportion of all of the above-mentioned vinyl esters in the polymer is preferably at least 50% by weight. The proportion of vinyl acetate in the total amount of vinyl esters in the copolymeric polyvinyl ester dispersion is preferably at least 50% by weight, in particular at least 75% by weight.

Other ethylenically unsaturated monomers which can be copolymerized with the vinyl esters are α,β-unsaturated acids, for example acrylic acid and methacrylic acid, and esters thereof with primary and secondary saturated monohydric alcohols having 1 to 18 carbon atoms, for example methanol, ethanol, propanol, butanol, 2-ethyl-hexyl alcohol, cycloaliphatic alcohols and longer-chain fatty alcohols. It is also possible to use, as additional monomers, α,β-unsaturated dicarboxylic acids, for example maleic acid, fumaric acid, itaconic acid or citraconic acid, and the mono- or diesters thereof with saturated monohydric aliphatic alcohols having 1 to 18 carbon atoms. The proportion of these comonomers in the total amount of monomers is up to 25% by weight, preferably from 0.1 to 15% by weight.

Further suitable comonomers are ethylenically unsaturated hydrocarbons, such as ethylene or α-olefins having 3–18 carbon atoms, for example propylene and butylene, and also styrene, vinyltoluene and vinylxylene, and halogenated unsaturated aliphatic hydrocarbons, for example vinyl chloride, vinyl fluoride, vinylidene chloride and vinylidene fluoride. The proportion of these comonomers in the total amount of monomers is up to 50% by weight, preferably from 1 to 25% by weight.

In addition, it is also possible for crosslinking, ethylenically polyunsaturated monomers to be present in the polymer during the polymerization, examples being diallyl phthalate, diallyl maleate, triallyl cyanurate, tetraallyloxyethane, divinylbenzene, 1,4-butanediol dimethacrylate, triethylene glycol dimethacrylate, divinyl adipate, allyl (meth)acrylate, vinyl crotonate, methylenebisacrylamide, hexanediol diacrylate, pentaerythritol diacrylate and trimethylolpropane triacrylate. The proportion of these comonomers in the total amount of monomers is up to 10% by weight, preferably from 0.01 to 2% by weight.

Particularly suitable comonomers are those with N-functional groups, including especially (meth) acrylamide, allyl carbamate, acrylonitrile, N-methylol (meth)acrylamide, N-methylolallyl carbamate and the N-methylol esters, N-alkyl ethers or Mannich bases of N-methylol(meth)acrylamide or N-methylolallyl carbamate, or else acrylamidoglycolic acid, methyl acrylamidomethoxyacetate, N-(2,2-dimethoxy-1-hydroxyethyl)acrylamide, N-dimethyl-aminopropyl(meth) acrylamide, N-methyl(meth)acrylamide, N-butyl(meth) acrylamide, N-cyclohexyl(meth)acrylamide, N-dodecyl (meth)acrylamide, N-benzyl(meth)acrylamide, p-hydroxyphenyl(meth)acrylamide, N-(3-hydroxy-2,2-dimethylpropyl)methacrylamide, ethylimidazolidone methacrylate, N-vinylformamide, N-vinylacetamide, N-methylol-N-vinylacetamide, N-vinylpyrrolidone, N-hydroxyethyl(meth)acrylamide, N-hydroxypropyl(meth)-acrylamide, N-methylolmaleamide, N-methylolmaleamic acid and esters thereof with aliphatic ($C_{1-C18}$) alcohols, and also the N-methylolamides of aromatic vinylcarboxylic acids, for example N-methylol-p-vinylbenzamide. The N-methylolamides of acrylic acid and methacrylic acid are particularly preferred when the dispersions prepared in accordance with the invention are to be used as water-resistant adhesives. The proportion of these comonomers in the total amount of monomers is up to 10% by weight, preferably from 0.1 to 5% by weight.

Further suitable comonomers are hydroxy-functional monomers, such as 2-hydroxyethyl (meth)acrylate, 3-hydroxypropyl (meth)acrylate and the adducts thereof with ethylene oxide or propylene oxide. The proportion of these comonomers in the total amount of monomers can be up to 10% by weight, preferably from 0.1 to 5% by weight.

Further suitable comonomers are those which possess autocrosslinking groups or groups which can be crosslinked via carbonyl groups, such as diacetoneacrylamide, allyl acetoacetate, vinyl acetoacetate and acetoacetoxyethyl (meth)acrylate. The proportion of these comonomers in the total amount of monomers is up to 10% by weight, preferably from 0.01 to 5% by weight.

The proportion of the comonomer units present in the polymer in addition to the vinyl ester units, taken together, is up to 50% by weight.

The homo- or copolymeric polyvinyl ester dispersion prepared in accordance with the invention is stabilized by protective colloids which are either placed in the aqueous polymerization liquor beforehand or are part introduced beforehand and part metered in during the polymerization or, in some cases, can also be added subsequently. The protective colloids used can be identical to or different from those present in the hydrosol which is employed. If the previously prepared hydrosol of the zirconium salt complexes is used complete, in a one-pot process, directly as polymerization liquor then the protective colloids already dissolved in the aqueous phase of the hydrosol, especially polyvinyl alcohol, have of course been introduced prior to polymerization. Moreover, it is of course also possible if required to add further protective colloids, especially polyvinyl alcohol, in the form of an aqueous solution prior to, gradually during, or after the polymerization reaction.

A preferred suitable compound for preparing and stabilizing the polyvinyl ester dispersion is polyvinyl alcohol, especially polyvinyl alcohol with a degree of hydrolysis of from 60 to 100 mol %, preferably from 70 to 98 mol %, and with viscosities of the 4% strength by weight aqueous solutions at 20° C. of from 2 to 70 mPa•s. It is also possible to employ functionalized polyvinyl alcohols as protective colloids. These are understood as being compounds which, either by subsequent reaction with appropriate compounds or by copolymerization with appropriate monomers, possess functional groups such as amino, carboxyl or acetoacetyl groups. Examples which may be mentioned are reaction products of polyvinyl alcohol with diketenes or copolymeric polyvinyl alcohols having crotonic acid or vinylamine units.

Other protective colloids which can be employed are etherified cellulose derivatives, for example hydroxyethylcellulose or carboxymethylcellulose, or polyvinylpyrrolidone, polyacrylic acid, copolymers of α-olefins with maleic acid, maleic acid derivatives or maleic anhydride, and copolymers of styrene and maleic acid, maleic acid derivatives or maleic anhydride. These are preferably used in combination with polyvinyl alcohol. Based on the solids content, the proportion of the polymeric protective colloids including the quantity of polyvinyl alcohol or other polymeric stabilizers already used to prepare the zirconium complex salt hydrosol is preferably from 1 to 20% by weight, in particular from 2 to 12% by weight.

It is also possible, in addition to the polymeric protective colloids, to use up to 3% by weight, including the quantity which may have already been used to prepare the hydrosol, and based on the polymer, of nonionic and/or ionic emulsifiers in the polymerization liquor.

The present invention provides, furthermore, a process for the preparation of the polyvinyl ester dispersion by continuous or discontinuous emulsion polymerization of at least one vinyl ester monomer and, if desired, further copolymerizable monomers in the presence of a hydrosol of a complex salt of metals from subgroup 4 of the Periodic Table of the Elements, especially zirconium, with an organic α-hydroxy and/or α-oxo acid, which hydrosol comprises a surface-active substance, preferably a predominantly polymeric stabilizer, especially polyvinyl alcohol.

In such a process, water-soluble and/or oil-soluble initiator systems are used, such as peroxodisulfates, azo compounds, hydrogen peroxide, organic hydroperoxides or dibenzoyl peroxide. These systems can be used either on their own or in combination with reducing compounds, such as Fe(II) salts, sodium pyrosulfite, sodium hydrogen sulfite, sodium sulfite, sodium dithionite, sodium formaldehyde-sulfoxylate or ascorbic acid as redox catalyst system. The use of a redox catalyst system, comprising for example tert-butyl hydroperoxide in combination with sodium formaldehyde-sulfoxylate, is preferred.

The reaction temperature during polymerization is from 20° to 100° C., in particular from 50° to 90° C. and, preferably, from 60° to 85° C.

Polymerization methods whose use is permitted are the common discontinuous or continuous procedures of free-radical emulsion polymerization. Preference is given, however, to the use of discontinuous processes such as batch processes, combined batch/feed processes or pure monomer feed processes. A pure monomer feed process is employed in particular. In this case, a small proportion (less than 10% by weight) of the monomers can be initially introduced into the polymerization liquor, which includes the hydrosol of zirconium complex salts, for the purpose of initial polymerization. The course of such a polymerization is preferably controlled such that there is no notable accumulation of monomer in the reactor.

Compared to seed polymerizations of conventional type, this process is also notable for its simplicity, and it is advantageous from a process safety standpoint since it involves a pure feed process.

The invention makes it possible, in a simple and safe procedure, presumably as a result of suppression of the aggregation of polymer particles during the polymerization, to have outstanding control over the rheology of the dispersions which are obtained as end products.

During the emulsion polymerization, the hydrosol aggregates are presumably broken down by processes which have not been investigated in more detail, the result of this breakdown being that there is no observed disruption to the properties of the dispersion when applied as a film.

The invention additionally provides for the use of the polyvinyl ester dispersions as coating or adhesive compositions especially as normal or water-resistant adhesives for porous or semiporous substrates, for example as wood adhesives or paper adhesives and for bonding press-molded laminates, reconstituted leather, and textiles. Their suitability lies preferably in sectors in which high shear stability and storage stability is a requirement of the end products in use.

In order to formulate the end products used as adhesives it is possible in addition to add customary additives to the polyvinyl ester dispersion, examples of these additives being film-forming auxiliaries for lowering the film-forming temperature (MFT), for example butyldiglycol acetate, and plasticizers, antifoams, fillers and preservatives.

If the dispersions prepared using crosslinkable or autocrosslinking comonomers, for example N-methylol (meth)acrylamide, are to be used as water-resistant adhesives with long pot lives, then, preferably, aqueous solutions of mineral acids with a $pK_a$ of <2.5, for example phosphoric acid, or acidic, water-soluble salts, for example aluminum chloride, aluminum nitrate or zirconium oxychloride, are additionally added as crosslinking catalysts. Thereafter, these adhesives meet the requirements for classification in at least strength class D2, preferably strength class D3, in accordance with the standard DIN EN 204.

The examples which follow serve to illustrate the invention. The parts and percentages indicated in the examples are by weight unless stated otherwise.

EXAMPLES

Preparation of complex salt hydrosols of Zr(IV) which are stabilized with polyvinyl alcohol Examples H1 to H7

Aqueous solutions each weighing 500 g and having the concentrations indicated in Table 1 are prepared with partially hydrolyzed polyvinyl alcohol with a degree of hydrolysis of 88 mol % and, in each case, the viscosities of the 4% strength aqueous solutions at 20° C. as shown in Table 1. 1.56 g (10.5 mmol) of glyoxylic acid (50% strength) are dissolved at 50° C. in each of these solutions, which are stirred using a paddle stirrer (100 rpm). After 10 minutes, 5.88 g (10.5 mmol Zr) of a commercial solution of zirconium acetate (22% strength based on $ZrO_2$) in each case are metered in over a period of 10 minutes. After a further 30 minutes, during which the batches take on a milky-cloudy consistency, they are cooled to room temperature.

The particle sizes of fresh samples of the hydrosols are determined by means of photon correlation spectroscopy. The values indicated for $d_z$ are the Z-mean values in the cumulative evaluation of the monomodal distribution (instrument: Malvern 4700, angle of scatter 90°; regarding the methodology of the measurement see also J. P. Fischer and E. Nölken, Progr. Colloid & Polymer Sci. 77, 180 (1988)). The ranges indicated delimit the measured Z-mean values of the particle sizes from in each case at least 2 reproduced batches.

TABLE 1

| Example | Visc. of a 4% strength aqueous solution of the PVA [mPa · s] ($M_w$ [g/mol]) | Conc. of the solution [%] | Mass PVA/ quantity Zr [g/mmol] | $d_z$ [µm] (range) | $d_z$ [µm] (mean) |
|---------|---------|---------|---------|---------|---------|
| H1 | 26 (160,000) | 1 | 0.5 | 2.1–3.0 | 2.5 |
| H2 | 26 (160,000) | 7 | 3.3 | 1.2–2.0 | 1.6 |
| H3 | 26 (160,000) | 13 | 6.2 | 0.8–1.4 | 1.1 |
| H4 | 4 (31,000) | 7 | 3.3 | 2.6–5.9 | 4.1 |
| H5 | 8 (67,000) | 7 | 3.3 | 2.6–4.2 | 3.6 |
| H6 | 18 (130,000) | 7 | 3.3 | 1.7–4.3 | 3.0 |
| H7 | 40 (205,000) | 7 | 3.3 | 0.9–2.0 | 1.4 |

On the basis of the progression in the ranges of the Z-mean values and in the mean values formed from the individual values (not shown here) it is evident that, both with increasing amounts of the stabilizer, polyvinyl alcohol, and—where equal quantities are used—with an increase in the viscosities of the 4% strength solutions and thus in the molecular weight of the polyvinyl alcohols, there is an increase in the finely divided nature of the hydrosols.

Preparation of polyvinyl acetate dispersions in the presence of complex salt hydrosols of Zr(IV) which are stabilized with polyvinyl alcohol Examples 1 and 2 and Comparison Examples V1, V2 and V3

1) Preparation of the polymerization liquors 3440 g of a 7% strength aqueous solution of partially hydrolyzed polyvinyl alcohol with a degree of hydrolysis of 88 mol % and a viscosity of the 4% strength aqueous solution of 26 mPa•s at 20° C. are initially charged to a 10 l glass reactor with anchor stirrer (110 rpm) which is furnished with metering devices, reflux condenser, jacket heating and jacket cooling.

In the case of Examples 1 and 2, these solutions are treated in analogy to the procedure of Example H2 with 10.65 g of glyoxylic acid (50% strength) and 40.32 g of zirconium acetate (22% $ZrO_2$). The pH of the hydrosols is subsequently adjusted from 3 to a value of 5 using 40.7 g of 10% strength NaOH. The batch is then used further directly in a one-pot process.

In the case of Comparison Examples V1 and V2 (customary procedure without treatment of the liquor) the polyvinyl alcohol solution is used as polymerization liquor without further treatment.

In the case of Comparison Example V3 (with acetate buffering), a pH of 3 is likewise established first of all with 16.56 g of acetic acid. A pH of 5 is then established with 74.3 g of 10% strength NaOH.

2) Emulsion polymerization

At an internal temperature of 50° C., 4 g of ®Agitan 280 (antifoam, Munzing-Chemie), 0.24 g of ®Rongalit C (sodium formaldehyde-sulfoxylate, BASF) dissolved in 33 g of water, and 200 g of vinyl acetate (5 parts) are added in succession to the liquor. The internal temperature is raised to 60° C. and the polymerization is initiated by adding a solution of 1.13 g of ®Trigonox AW 70 (tert-butyl hydroperoxide, 70% pure, Akzo-Chemie) in 20 g of water.

After complete polymerization of the initial charge (internal temperature 68° C.), two or three feeds consisting on the one hand of 3840 g (95 parts) of vinyl acetate with 3.5 g of Trigonox AW 70 in the case of Examples 1 and V1 or 3760 g (93 parts) of vinyl acetate with 3.5 g of Trigonox AW 70 in addition to 166.7 g (2 parts) of N-methylolacrylamide (48% strength) in 400 g of water in the case of Examples 2, V2 and V3 and, on the other hand, 1.2 g of Rongalit C in 400 g of water are metered in over the course of 3 hours. The jacket temperature is controlled such that the polymerization takes place without reflux at a slowly increasing internal temperature of 68° C. at the start to about 80° C. Post-polymerization is then carried out with subsequent additions of solutions of 0.57 g of Trigonox AW 70 and 0.18 g of Rongalit C in 10 g and, respectively, 80 g of water. After cooling, 160 g of butyldiglycol acetate are stirred slowly into the dispersion in order to reduce the MFT.

Analysis of the dispersions

1. Viscosities: Brookfield RVT (7/20), 23° C.

2. The thixotropic area is determined in a rotary viscometer of the Rheomat 115 type from Contraves in the shear range of D=20 to 1000 s$^{-1}$. Measurement conditions: duration of the upward curve: 1 minute, holding time at D=1000 s$^{-1}$: 5 minutes, duration of the downward curve: 1 minute.

3. The particle-size distributions are analyzed by means of the method, described in the literature, of Xe laser aerosol spectroscopy (Xe-LAS): J. P. Fischer in FH Texte der Fachhochschule Aachen, vol. 66 (1995), and literature cited therein (for example Kunstharz Nachrichten 28, 12 ff. (1991).

TABLE 2

Analytical data of the dispersions

| Example | Comonomer | Solids content [%] | pH | Viscosity [Pa · s] | Thixotropic area [MPa · s] |
|---------|-----------|---------|-----|---------|---------|
| 1 | — | 52.7 | 4.5 | 33 | 0.23 |
| V1 | — | 52.2 | 3.8 | 102 | 2.18 |
| 2 | 2% NMA | 49.6 | 4.5 | 15 | 0.18 |
| V2 | 2% NMA | 50.2 | 3.9 | 78 | 3.19 |
| V3 | 2% NMA | 50.1 | 4.9 | 53 | 1.01 |

As is evident from this Table, Examples 1 and 2 according to the invention are distinguished, each having a very low thixotropic area, by an extremely high shear stability and, at comparable solids contents, by a markedly lower viscosity in comparison with Examples V1 and, respectively, V2 and V3. Purely by means of acetate buffering, which likewise exerts a positive effect, as in Example V3, it is not possible to bring about this effect. The reason for this characteristic lies in differences in the particle-size distributions.

TABLE 3

Analysis of the particle-size distributions

| Example | Light microscopy | Xe-LAS: $d_w$ (range) |
|---|---|---|
| 1 | predominantly individual particles, plus a few aggregates | bimodal distribution 0.4–0.8 µm (i.p.) plus 1.5–3 µm (agg.) |
| V1 | few individual particles predominantly particle aggregates | bimodal distribution 0.3–0.6 µm (i.p.) plus 0.9–3 µm (agg.) |
| 2 | predominantly individual particles, plus relatively small aggregates | bimodal distribution 0.4–0.8 µm (i.p.) plus 1.5–3 µm (agg.) |
| V2 | predominantly particle aggregates | 1.5–4 µm (agg.) |
| V3 | predominantly particle aggregates | 1.5–4 µm (agg.) |

Examples 2-A and Comparison Examples V2-A and V3-A

Testing of the copolymeric polyvinyl acetate dispersions in combination with an acid curing agent as water-resistant wood adhesives 27 parts by weight of a 28% strength solution of aluminum chloride in water are stirred into 1000 parts by weight of each of the dispersions of Examples 2, V2 and V3. The adhesives characteristics are determined on the basis of the test standard DIN EN 204 (previously DIN 68602). The test specimens required for this test are prepared in accordance with the procedure of DIN EN 205 (previously DIN 53254). Gluing and testing are carried out under the following conditions:

| | |
|---|---|
| Glue application: | 150 ± 20 g/m² applied to both sides |
| Open waiting time: | 3 minutes |
| Closed waiting time: | 3 minutes |
| Compression time: | 2 hours |
| Pressure of compression: | 0.7 ± 0.1 N/mm² |
| Number of test specimens per test series: | 20 |
| Testing after: | |
| Storage cycle according to DIN EN 204 D1/1: | 7 days standard conditions*) |
| Storage cycle according to DIN EN 204 D3/3: | 7 days standard conditions 4 days in cold water |
| Storage cycle according to D1/80° C.: (not part of DIN EN 204) | 7 days standard conditions 2 hours in oven at 80° C. (Testing at 80° C.) |
| Test temperature: | 23° C. ± 2° C. |
| Rate of advance: | 50 mm/min. |

*)23 ± 2° C. and 50 ± 5% relative atmospheric humidity

Allocation to strength class D1/1 is awarded for a tear strength of $\geq 10$ N/mm².
Allocation to strength class D3/3 is awarded for a tear strength of $\geq 2$ N/mm².
Determination of pot life following addition of curing agent In the storage experiment at room temperature, this time is taken to be the period during which the adhesive dispersion, following addition of curing agent, is still readily flowable, with a viscosity of $\geq 75$ Pa•s by Brookfield RVT 7/20, and after which time it meets the standard adhesives values.

The test data obtained are listed in Table 4 below. They show that both Example 2-A of the process according to the invention and the Comparison Examples meet the standard test values required. Example 2-A is distinguished, moreover, by a dramatic increase in the pot life. All of the standard test values continue to be met after a period of 2 months.

TABLE 4

| Example | 2-A | V2-A | V3-A |
|---|---|---|---|
| Visc. Brookfield RVT 7/20 start [Pa · s] | 9 | 64 | 47 |
| D1/1 [N/mm²] | 15.8 | 15.4 | 16.9 |
| D1/80° C. [N/mm²] | 8.3 | 8.4 | 8.5 |
| D3/3 [N/mm²] | 3.5 | 4.5 | 5.1 |
| Pot life | >>6 weeks | <14 days | <14 days |
| D1/1 after 2 months [N/mm²] | 16.9 | — | — |
| D1/80° C. after 2 months [N/mm²] | 7.8 | — | — |
| D3/3 after 2 months [N/mm²] | 5.8 | — | — |

We claim:

1. A hydrosol of a complex salt of a metal from subgroup 4 of the Periodic Table of the Elements with an organic α-hydroxy and/or α-oxo acid, which hydrosol comprises a surface-active substance.

2. A hydrosol as claimed in claim 1, wherein the organic acid is a mono- or polyfunctional carboxylic acid which, in the α-position to at least one carboxyl group, has a carbonyl group which in the aqueous phase at equilibrium is in completely or partially hydrated form.

3. A hydrosol as claimed in claim 1, wherein the organic acid is glyoxylic acid.

4. A hydrosol as claimed in claim 1, wherein the metal from subgroup 4 is zirconium.

5. A hydrosol as claimed in claim 1, wherein the surface-active substance is polyvinyl alcohol.

6. A process for the preparation of a hydrosol of a complex salt of a metal from subgroup 4 of the Periodic Table of the Elements with an organic α-hydroxy and/or α-oxo acid as claimed in claim 1 by precipitation, from homogeneous aqueous solution, of water-soluble salt of the metal by adding an organic α-hydroxy and/or α-oxo acid or an aqueous or organic solution of the organic acid in the presence of a surface-active substance.

7. A polyvinyl ester dispersion which is obtainable by emulsion polymerization of at least one vinyl ester monomer and, if desired, further copolymerizable monomers in the presence of a hydrosol of a complex salt of a metal from subgroup 4 of the Periodic Table of the Elements with an organic α-hydroxy and/or α-oxo acid, which hydrosol comprises a surface-active substance.

8. A process for the preparation of a polyvinyl ester dispersion by continuous or discontinuous, free-radical emulsion polymerization of at least one vinyl ester monomer and, if desired, further copolymerizable monomers in the presence of a hydrosol of a complex salt of a metal from subgroup 4 of the Periodic Table of the Elements with an organic α-hydroxy and/or α-oxo acid, which hydrosol comprises a surface-active substance.

9. A polyvinyl ester dispersion as claimed in claim 7, wherein vinyl acetate is employed as vinyl ester monomer.

10. A polyvinyl ester dispersion as claimed in claim 7, wherein an autocrosslinking or subsequently crosslinkable monomer is employed as further copolymerizable monomer.

11. The use of a polyvinyl ester dispersion as claimed in claim 7 as an adhesive or coating composition.

* * * * *